(12) United States Patent
Doucette et al.

(10) Patent No.: US 8,372,183 B2
(45) Date of Patent: Feb. 12, 2013

(54) DETECTION SYSTEM FOR AIRBORNE PARTICLES

(75) Inventors: Luke D. Doucette, Hampden, ME (US);
Carl P. Tripp, Orono, ME (US); Brian J. Ninness, Hampden, ME (US)

(73) Assignees: Orono Spectral Solution, Inc., Orono, ME (US); University of Maine System Board of Trustees, Bangor, ME (US)

( * ) Notice: Subject to any disclaimer, the term of this patent is extended or adjusted under 35 U.S.C. 154(b) by 1645 days.

(21) Appl. No.: 11/811,833

(22) Filed: Jun. 12, 2007

(65) Prior Publication Data

US 2012/0274933 A1    Nov. 1, 2012

(51) Int. Cl.
*B03C 3/34* (2006.01)
(52) U.S. Cl. .............. 96/19; 73/864.71; 95/3; 96/26
(58) Field of Classification Search .......... 96/18, 19, 96/26; 95/2, 3; 73/28.02, 864.71
See application file for complete search history.

(56) References Cited

U.S. PATENT DOCUMENTS

| | | | |
|---|---|---|---|
| 1,120,560 A * | 12/1914 | Strong | 96/19 |
| 3,700,330 A | 10/1972 | Davis | |
| 3,970,428 A | 7/1976 | Barringer | |
| 4,038,049 A * | 7/1977 | Melcher et al. | 95/62 |
| 4,590,792 A | 5/1986 | Chiang | |
| 4,924,097 A | 5/1990 | Browner et al. | |
| 4,942,297 A | 7/1990 | Johnson et al. | |
| 5,117,190 A | 5/1992 | Pourprix | |
| 5,133,519 A | 7/1992 | Falco | |
| 5,254,861 A | 10/1993 | Carpenter et al. | |
| 5,316,983 A * | 5/1994 | Fujimori et al. | 356/335 |
| 5,442,190 A | 8/1995 | Leck | |
| 5,679,137 A * | 10/1997 | Erdman et al. | 96/26 |
| 5,932,795 A | 8/1999 | Koutrakis et al. | |
| 5,938,823 A | 8/1999 | Condit et al. | |

(Continued)

FOREIGN PATENT DOCUMENTS

DE    10309518 A1    9/2004
WO    00/14674    3/2000

(Continued)

OTHER PUBLICATIONS

Department of Defense Publication, "Realtime Detection and Identification of Airborne Microorganisms Using Infrared Spectroscopy," Jun. 13, 2006 (abstract).

(Continued)

*Primary Examiner* — Richard L Chiesa
(74) *Attorney, Agent, or Firm* — MacMillan, Sobanski & Todd, LLC

(57) ABSTRACT

This invention relates to a detection system for particles suspended in a gas. The detection system includes an electrostatic precipitator constructed to collect the particles from the gas onto a collection surface using the force of an induced electrostatic charge on the particles. The detection system also includes an optical probe coupled with the electrostatic precipitator and constructed to probe the particles with a beam in order to detect the particles. The body of the electrostatic precipitator has a geometry that allows the beam to travel from the optical probe to the collection surface.

23 Claims, 4 Drawing Sheets

U.S. PATENT DOCUMENTS

| | | | |
|---|---|---|---|
| 5,993,738 A | 11/1999 | Goswani | |
| 6,043,639 A | 3/2000 | Arrowsmith et al. | |
| 6,323,633 B1 | 11/2001 | Kinne | |
| 6,511,854 B1 | 1/2003 | Asanov et al. | |
| 6,787,104 B1 | 9/2004 | Mariella, Jr. | |
| 7,041,153 B2 * | 5/2006 | Totoki | 95/3 |
| 7,082,369 B1 | 7/2006 | Rubin et al. | |
| 2003/0136205 A1 | 7/2003 | Totoki | |
| 2005/0190058 A1 | 9/2005 | Call | |
| 2006/0081127 A1 * | 4/2006 | Totoki | 96/18 |

FOREIGN PATENT DOCUMENTS

| | | |
|---|---|---|
| WO | 2007009863 A2 | 1/2007 |
| WO | 2007011726 A1 | 1/2007 |

OTHER PUBLICATIONS

Department of Defense Publication, "Reagentless and Realtime Detection of Airborne Microoragisms," Jun. 5, 2006 (abstract).

* cited by examiner

DETECTION SYSTEM FOR AIRBORNE PARTICLES

STATEMENT OF GOVERNMENT FUNDING

This invention was made at least in part using government funding under Department of Defense Contract Nos. W911SR06C0029 and W911SR07C0039. The U.S. Government may have rights herein.

BACKGROUND OF THE INVENTION

Currently there exists a critical need within the military and homeland defense for sensors and detection systems that are capable of identifying and quantifying airborne microorganisms and biowarfare agents. In addition, monitoring of airborne particulates generated from industrial activities is a persistent concern within private and public settings. In general, bacterial and fungal spores are the predominant microorganisms that exist in air as aerosols. In order to reliably detect and identify small quantities of bioaerosols, a real-time detection system exhibits both high sensitivity and the ability to discriminate between potential threat agents and interfering substances present in the environment.

For a complete bioaerosol detection system, the four basic components are the trigger, collector, detector and identifier. The trigger determines a change in the particulate background and initiates operation of the remaining components of the system. The collector is a necessary component as the effective lethal dose of biological agents is extremely low (8,000-10,000 inhaled spores for *Bacillus anthracis*). The detector determines if the particulates are of biological origin, and the identifier specifically identifies the type of biological agent. Therefore, a real-time detection system includes both sampling/concentrating and identification in the same instrument.

An abstract published by Orono Spectral Solutions, Inc. entitled "Realtime Detection and Identification of Airborne Microorganisms Using Infrared Spectroscopy" discloses a detection system that couples an electrostatic precipitator for collecting airborne microorganisms with an infrared spectrometer for detecting and identifying the microorganisms.

An abstract published by Lynntech, Inc. entitled "Reagentless and Realtime Detection of Airborne Microorganisms" discloses a detection system that uses electrostatic precipitation to capture and preconcentrate biological agents and spores directly on a reusable infrared transparent crystal followed by infrared spectroscopic characterization.

U.S. Pat. No. 5,254,861 entitled "Biological Aerosol Particle Detector and Method Having an Electronic Pulse Detection Means" claims a system to detect airborne biological particles which first ionizes the particles with low energy radiation and then passes them between two electrically charged conducting plates. In one embodiment, an infrared laser diode and photodiode are added to characterize the biological particles based upon particle charge and drift velocity.

It would be desirable to provide an improved detection system for airborne particles.

SUMMARY OF THE INVENTION

This invention relates to a detection system for particles suspended in a gas. The detection system includes an electrostatic precipitator constructed to collect the particles from the gas onto a collection surface using the force of an induced electrostatic charge on the particles. The detection system also includes an optical probe coupled with the electrostatic precipitator and constructed to probe the particles with a beam in order to detect the particles. The body of the electrostatic precipitator has a geometry that allows the beam to travel from the optical probe to the collection surface.

In one embodiment, the electrostatic precipitator includes first and second electrodes. Specifically, in one embodiment one or both of the electrodes has a structure that causes deposition of the particles in a defined area on the collection surface. More specifically, the defined area substantially matches a cross-sectional area of the probe beam.

In another embodiment, the detection system allows continuous or semi-continuous collection and detection of the particles. Specifically, in one embodiment the collection surface is separate from the electrostatic precipitator body to allow the collection and detection to be spatially decoupled. In another specific embodiment, the collection surface is moveable relative to the electrostatic precipitator body to allow the collection and detection of the particles to occur at different sections along the collection surface.

Various aspects of this invention will become apparent to those skilled in the art from the following detailed description of the preferred embodiments, when read in light of the accompanying drawings.

DETAILED DESCRIPTION OF THE PREFERRED EMBODIMENTS

Figure 1:
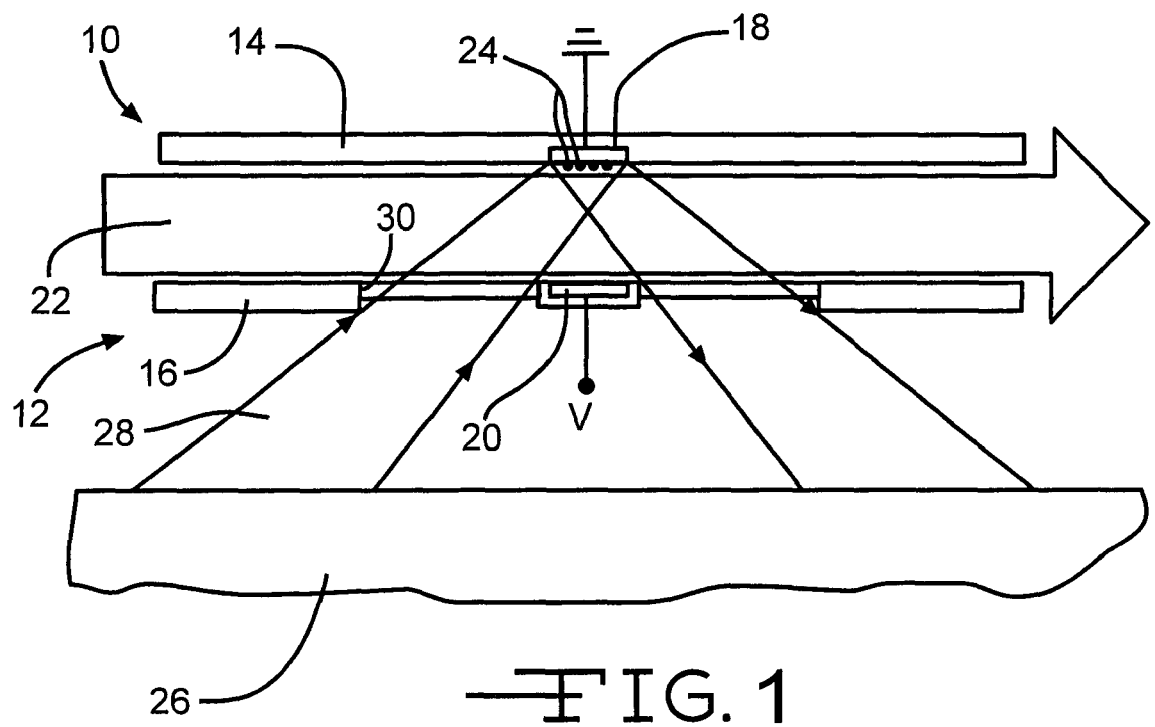
FIG. 1 is a diagram of a detection system according to the invention including an electrostatic precipitator parallel plate collector and an infrared (IR) probe. The system uses an IR beam reflection-absorption mode for detection of particles.

The present detection system is suitable for collecting and detecting many different kinds of particles suspended in a gas. In one embodiment, the detection system is used with an aerosol, which consists of tiny particles or particulates suspended in a gas. The particulates can have many different origins. For example, they can be generated from industrial activities, or they can be of biological origin. In one embodiment, the detection system is able to detect any aerosolized particles including organic or inorganic particles. Some examples of biological particulates include airborne microorganisms and bio-warfare agents. Bacterial and fungal spores are the predominant microorganisms that exist in the air as aerosols. Some specific examples are spores of *bacillus*

*anthracis* and spores of *bacillus globigii*. The gas can be air or any other gas, or mixture of gases, suitable for suspending the particulates.

The detection system includes an electrostatic precipitator constructed to collect the particles from the gas onto a collection surface using the force of an induced electrostatic charge on the particles. Conventional electrostatic precipitators are well known in the art and consequently the details of their structure and operation will not be repeated here. Basically, the electrostatic precipitator electrically charges the gasborne particles, subjects them to a strong electric field, and then collects them onto a collection surface by electrostatic attraction. In many embodiments, the electric field is created between spaced apart electrodes and the particles are attracted to one of the electrodes. For example, one of the electrodes may be charged and the other grounded or the electrodes may be oppositely charged. Some examples of different types of electrostatic precipitators include plate precipitators, modern industrial electrostatic precipitators and wet electrostatic precipitators. One-stage electrostatic precipitators both charge the particles and collect them in the same stage, while two-stage electrostatic precipitators charge the particles in a first stage and collect them in a second stage.

The detection system also includes an optical probe coupled with the electrostatic precipitator and constructed to probe the particles with a beam in order to detect the particles. The structure and operation of optical probes are well known in the art and thus will not be repeated here. Any type of optical probe capable of functioning as described herein can be used as part of the detection system. For example, in one embodiment the optical probe is selected from near, mid and far infrared probes, Raman probes using lasers from the ultraviolet to the near infrared region, ultraviolet light probes, visible light probes, fluorescent light probes, terahertz light probes, and laser probes. In a specific embodiment, the optical probe is an infrared probe such as an infrared spectrometer. In one embodiment, the optical probe is able to identify the particles that are detected. The optical probe may include or may be coupled to a device or system to facilitate the detection and/or identification functions; for example, it may be coupled to a linear operator such as Fourier Transform or to a dispersive based or laser based system.

The body of the electrostatic precipitator has a geometry that allows the beam to travel from the optical probe to the collection surface. This can be accomplished in any suitable manner, for example, by modifying the geometry of a conventional electrostatic precipitator. In one embodiment, the geometry allows the beam to travel directly from the optical probe to the collection surface. The beam may probe the particles on the collection surface in a reflection mode or a transmission mode, as described in more detail below. In one embodiment, the structures of the electrostatic precipitator and the optical probe cooperate to allow real-time or near real-time detection of the particles. More specifically, the geometry of a conventional electrostatic precipitator may be modified to include the ability to directly probe the collection surface via optical detection methods in real or near real-time.

The electrostatic precipitator can have any suitable geometry that allows the beam to travel from the optical probe to the collection surface. In one embodiment, the geometry includes an access structure that allows the beam to travel through or around the body. Some examples of access structures include windows or screens in the body, and solid materials in the body through which the beam can travel. In another embodiment, the electrostatic precipitator body is shaped or contoured to allow the beam to travel to the collection surface.

Various electrostatic precipitator geometries are illustrated in FIGS. 1-4, which show how optical analysis of the collected particles can be performed in reflection or transmission modes.

FIG. 1 illustrates a detection system 10 including an electrostatic precipitator 12. The body of the electrostatic precipitator includes first and second insulators 14 and 16 in the form of parallel plates. The insulators are made from any suitable electrical insulating material, such as porcelain, alumina or silica.

The electrostatic precipitator also includes first and second parallel plate electrodes 18 and 20 mounted inside the insulators. The first electrode is grounded while the second electrode is charged. In the embodiment shown, the first electrode 18 is a collector electrode that functions as the collection surface of the electrostatic precipitor. For the collector electrode, virtually any metal (e.g. gold, aluminum, copper, silver, iron, platinum, palladium, etc.), alloy (e.g. steel, indium tin oxide), or metal coated dielectric material (e.g. polymers, plastics, ceramics) could be utilized in order to achieve high collection and reflection efficiency with minimal loss of IR signal.

An air stream 22 with suspended charged particles flows between the insulators and the electrodes. The particles in the air stream have been charged in any suitable manner (not shown), for example by corona, UV, nuclear radiation, or triboelectric charging, or via chemical reaction. The voltage bias between the electrodes causes the charged particles 24 to precipitate from the air stream and concentrate on the inner surface of the collector electrode 18.

The detection system also includes an infrared spectrometer 26 coupled with the electrostatic precipitator. In one embodiment an infrared laser could be used. The infrared spectrometer sends out an infrared beam 28 to probe the collected particles 24 on the surface of the collector electrode 18. The insulator 16 includes an access structure in the form of a window 30 that allows the beam 28 to travel directly from the infrared spectrometer to the surface of the collector electrode 18. In one embodiment, the area of the surface of the collector electrode is throughput matched to the cross-sectional area of the beam to optimize signal-to-noise in order to achieve low detection limits.

The beam 28 contacts the surface of the collector electrode 18 and is absorbed differently by the collected particles 24 depending on their identity. The beam is then reflected from the collector electrode and travels back through the window to a detector of the infrared spectrometer. This reflection-absorption infrared spectroscopy is used to generate a spectrogram that identifies the collected particles. Typically, when this type of spectroscopy is used, the beam is reflected off the collector electrode at a relatively high incidence angle.

Figure 2:
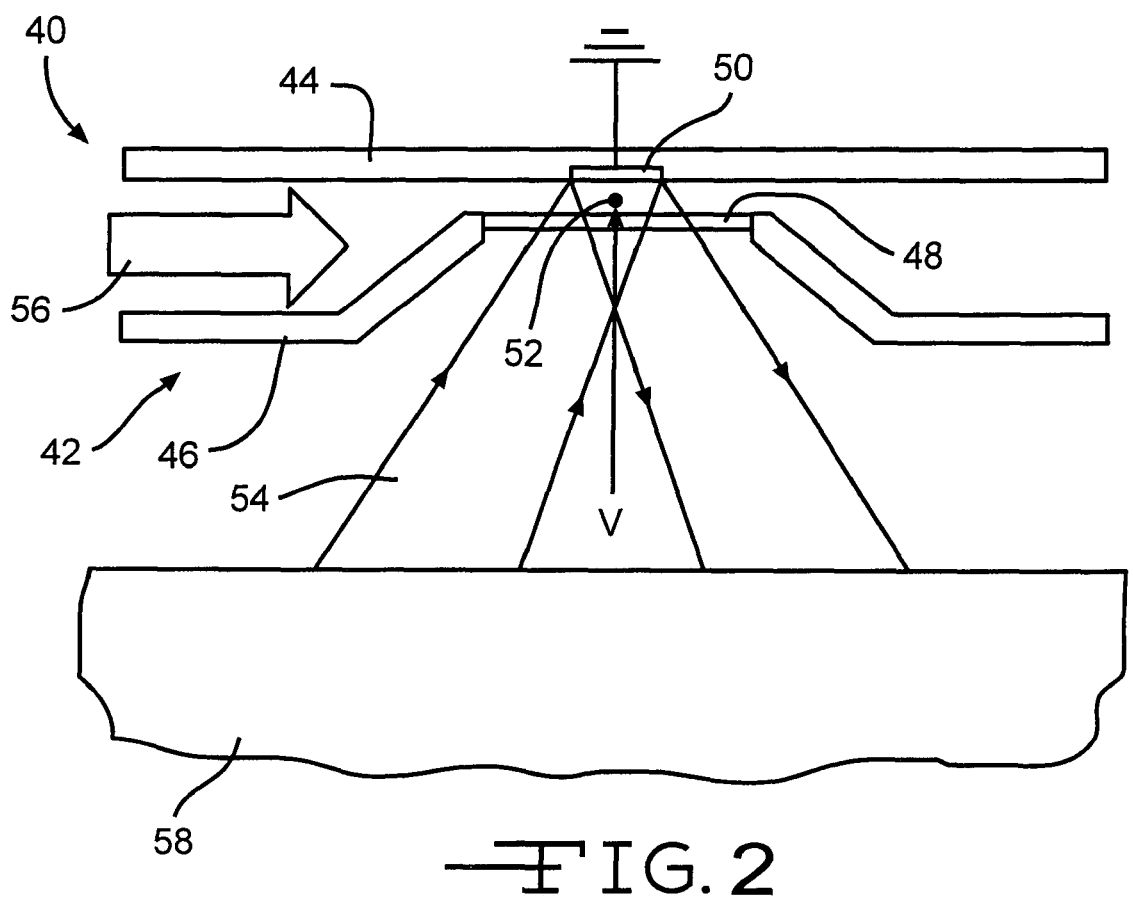
FIG. 2 is a diagram of a detection system including an electrostatic precipitator wire/grid collector and an IR probe. The system uses an IR beam reflection-absorption mode for detection of particles.

FIG. 2 illustrates a detection system 40 including an electrostatic precipitator 42. The body of the electrostatic precipitator includes a first insulator 44 in the form of a plate and a parallel second insulator 46 in the form of a plate having a necked in central portion. The central portion of the second insulator has a window 48 through which the beam can travel.

The electrostatic precipitator includes a first plate electrode 50 which is grounded. The first electrode functions as a collector electrode. The electrostatic precipitator also includes a wire or wire grid as the second electrode 52 which is charged. Although the presence of the wire 52 will obstruct a portion of the infrared beam 54, this effect can be made negligible by utilizing a sufficiently thin wire. The advantage of this type of structure is that highly localized electric fields produced between the wire 52 and the collector electrode 50 enables particles to be collected into a smaller area, which facilitates lower detection limits when this area is through-put matched with the infrared beam.

More generally, in one embodiment of the detection system at least one of the electrodes has a structure that causes deposition of the particles in a defined area on the collection surface. For example, one or both of the electrodes may be a single wire, grid, or any configuration of single wires that enables deposition of the spores in a defined region on the collection surface. The electrode(s) can have any structure that facilitates the collection of the particles into a small area, for example an area not greater than about 5 cm². In addition to the wire(s) or grid, examples of other possible structures include a needle, an arrangement of needles, a knife edge, or cylinder(s).

The purpose of this electrode structure is to intensify and localize the electric field between the electrodes in order to facilitate particle collection into a smaller, more concentrated area on the collection surface. When this collection area is throughput matched with an optical probe beam, the detection signal increases as the area decreases for the same mass of sample according the Beer-Lambert relationship:

$$\text{Absorbance} = \varepsilon \times \frac{\text{Mass}}{\text{Area}}$$

where $\varepsilon$ is the extinction coefficient of the material which is constant. Therefore, concentrating the collected particles into a smaller area and throughput matching this collection area with an optical probe beam produces a larger signal for the same amount of particles, which effectively reduces the overall detection limit provided by the detection system.

Referring again to FIG. 2, an air stream 56 with suspended charged particles flows between the insulators and the electrodes. The voltage bias between the electrodes causes the charged particles to precipitate from the air stream and concentrate on the inner surface of the collector electrode 50.

The detection system 40 also includes an infrared spectrometer 58 coupled with the electrostatic precipitator 42. The infrared spectrometer sends out an infrared beam 54 to probe the collected particles on the surface of the collector electrode 50. The beam travels through the window 48 in the second insulator 46. The beam contacts the surface of the collector electrode and is absorbed differently by the collected particles depending on their identity. The beam is then reflected from the collector electrode and travels back through the window to a detector of the infrared spectrometer. A spectrogram is generated that identifies the collected particles.

Figure 3:
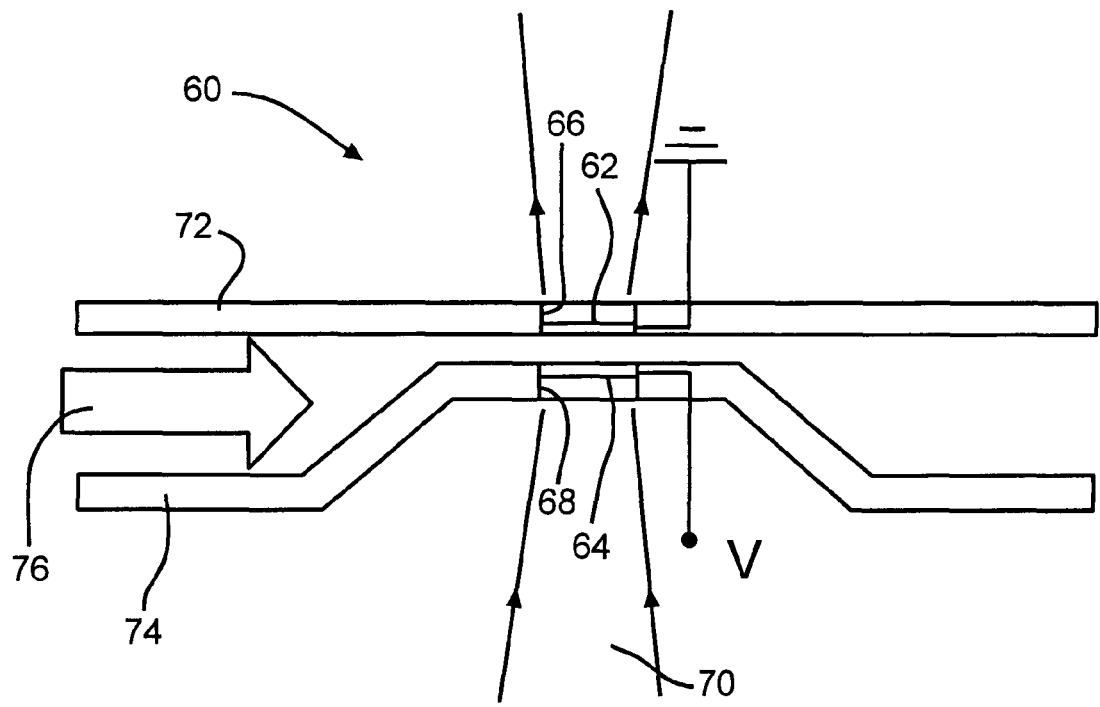
FIG. 3 is a diagram of a detection system including an electrostatic precipitator parallel plate collector and an IR probe. The system uses an IR beam transmission mode for detection of particles.

FIG. 3 shows a third detection system 60 that utilizes infrared transparent, thin metal film electrodes 62 and 64 deposited onto infrared windows 66 and 68 in the collection region. The electrode 62 is a collector electrode. A sufficiently thin metal film will not significantly attenuate an infrared beam 70 propagating through the metal film/window system. In this arrangement, infrared transmission spectra of the collected particles can be continuously acquired by sampling through the parallel plate collector as shown in the figure. An advantage of this design is in its simplicity and small working distance between electrodes. Like the previous designs, this detection system includes first and second insulators 72 and 74. An air stream 76 containing dispersed charged particles flows between the insulators and the electrodes.

Figure 4:
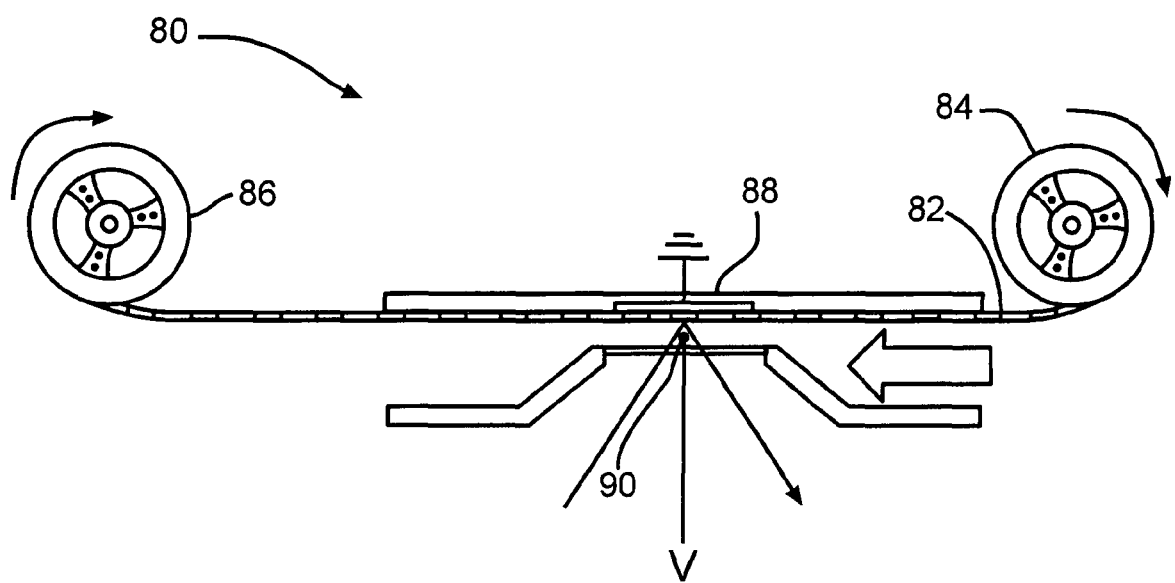
FIG. 4 is a diagram of a detection system including an optical probe and an electrostatic precipitator collector that uses rolling tape for a collection surface.

For continuous (or semi-continuous) collection and detection, fixed electrode collector plates may require some form of interruption in operation in order to clean the collection surface once the surface has been sufficiently fouled with collected particles. FIG. 4 shows a detection system 80 in which the collection surface is not fixed, but consists of a rolling tape 82 which allows for collection and detection to occur at different sections along the tape. The tape 82 is played out from a feed roll 84 and pulled onto a receiving roll 86. The tape can be any suitable material, for example a thin metal (e.g. aluminum, steel, etc.), mylar, or essentially any material capable of being wound. The collection period for a given section of tape would be based upon either a predetermined fixed period of time, or real-time monitoring of changes in the detection signal before triggering to a new section. The electrostatic precipitator structure could include the tape serving as one of the operating electrodes, or the tape could pass between electrodes that are parallel plate, wire/plate, or wire/wire designs. In the embodiment shown, the tape 82 passes between a plate electrode 88 and a wire electrode 90. Optical analysis of the collected particles could be accomplished during collection (like shown in FIG. 4) or separate from the collection region at a different location once the tape has triggered to a new section. In addition to resolving collector plate fouling and providing semi-continuous collection and detection capabilities, the collection tape would also serve as a physical archive of the collected particles, which could be reprocessed for later validation testing.

More generally, in one embodiment the detection system includes a collection surface that is separate from the electrostatic precipitator body to allow the collection and detection to be spatially decoupled. In one embodiment the collection surface is moveable relative to the electrostatic precipitator body to allow the continuous or semi-continuous collection and detection of the particles to occur at different sections along the collection surface. Any suitable moveable collection surface can be used, for example a rolling tape, a rotating disk, a moveable plate, or any other structure that is moveable relative to the electrostatic precipitator body. Collection and detection may occur simultaneously (continuous detection), where the collection surface is moved to a "clean" area once a given collection area has been sufficiently fouled; or collection and detection may be spatially decoupled such that the moveable collection surface moves the collected sample from the collection region to a separate detection region (semi-continuous).

EXPERIMENTAL

Prototype Design

Figure 5:
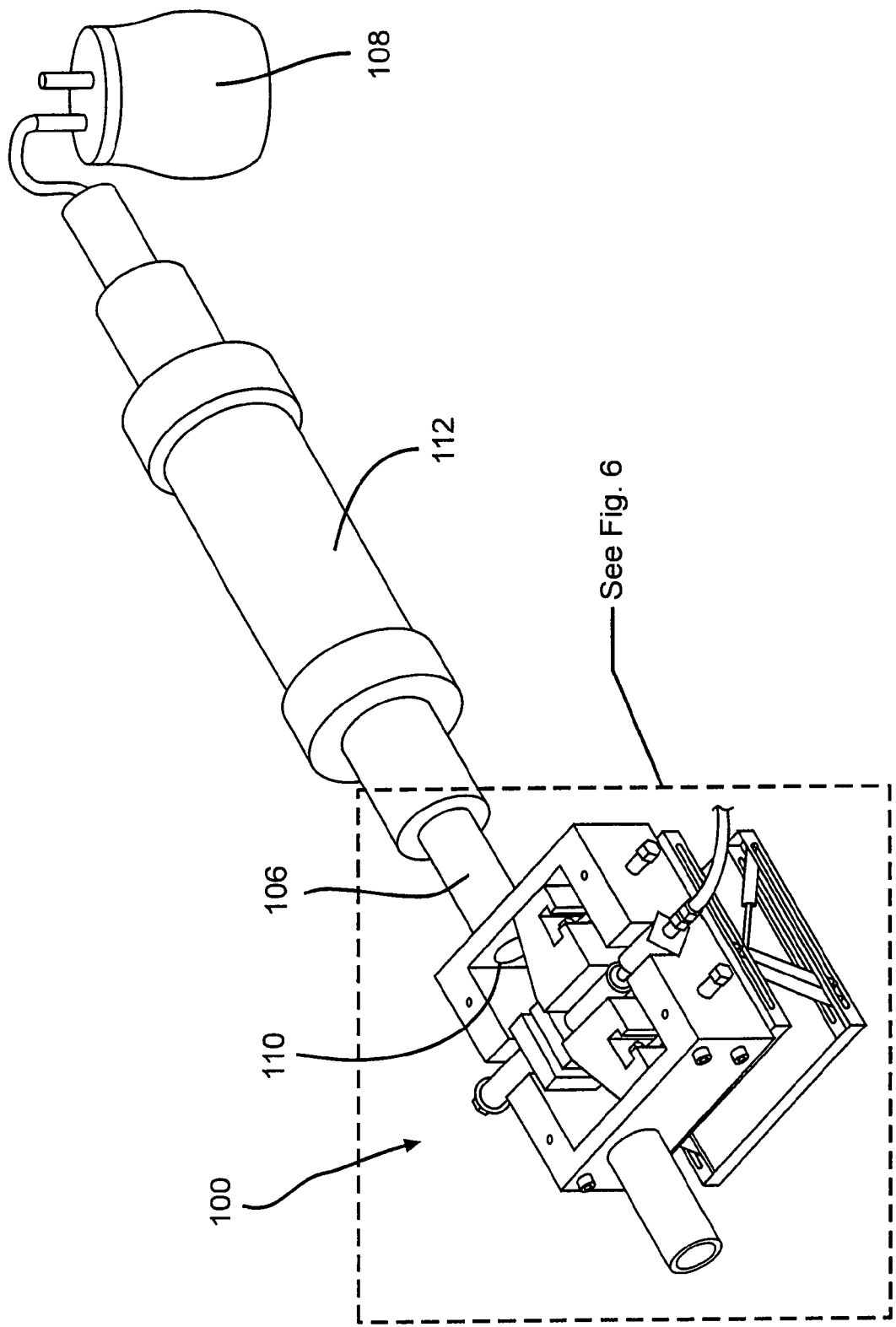
FIG. 5 is a perspective view of an electrostatic precipitator collector for use in a detection system according to the invention.
Figure 6:
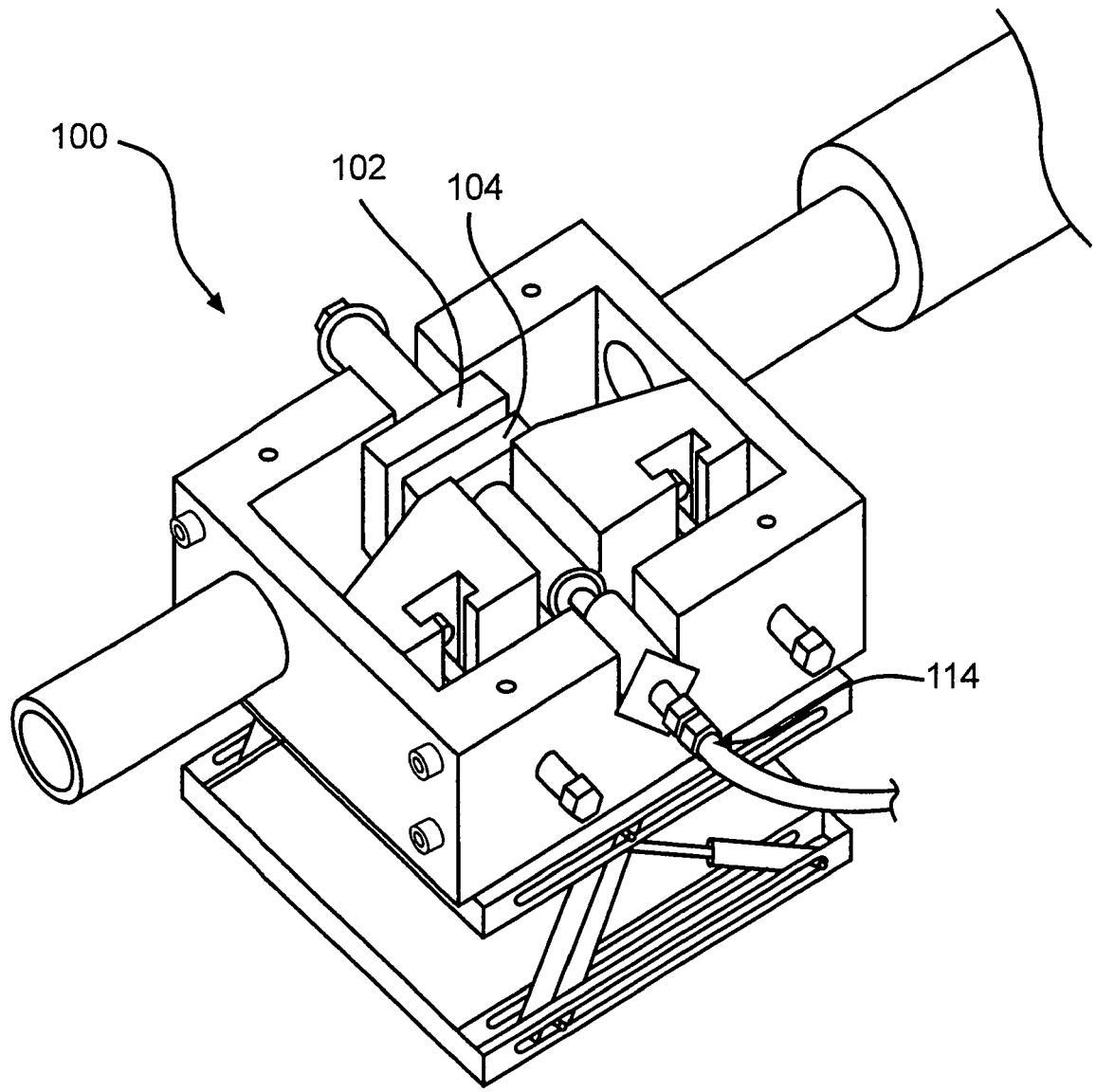
FIG. 6 is a perspective view of an electrostatic precipitator collector for use in a detection system according to the invention, and associated apparatus for the generation of an aerosol including biological particles that are collected and detected by the system.

To concentrate aerosolized spores, we designed and constructed the electrostatic precipitator (ESP) collector cell 100 shown in FIGS. 5 and 6. For this particular design, the collection region consists of a set of removable parallel plates 102 and 104 that are each 1 inch². The gap between the plates was adjustable from 0 to 1 inch. Teflon sheets and tubing were used to insulate the polished stainless steel plates and electrode pins from the rest of the cell housing, which is also constructed of stainless steel and grounded during tests. Grounded conductive silicone tubing 106 was used to connect the nebulizer 108 to the cell inlet 110 to ensure aerosol flow through the cell. The conductive tubing and cell housing were grounded so as to prevent localized charge regions from developing and possibly serving as unintended collection sites. For all results discussed, reflection-absorption (R-A) IR spectral analysis of the removable collector plates was performed by removing the collector plates post collection and placing them into an R-A optical assembly mounted onto a mid IR Laboratory Analyzer with an MCT detector (ABB FT-IR FTLA2000).

Bioaerosol Generation and Delivery System

FIG. 5 shows the entire bioaerosol generation and delivery system utilized for our experiments, with an inset showing the ESP cell 100 with the top cover off. Test aerosols were generated and contained within a Class III glove box (Labconco Model 50350). For spore aerosolization, we utilized a 3 jet Collison nebulizer 108 (BGI, Waltham, Mass.) which is capable of producing air flows ranging from 3 to 21 LPM. BG spores obtained from Dugway Proving Grounds, UT, were used with the nebulizer for testing purposes. To control the relative humidity (RH) of the aerosolized spore stream entering the ESP collection cell, an inline diffusion drier 112 was built and added to the delivery system. Our results show that controlling the RH significantly affects the collection efficiency of the ESP cell, and these results are discussed in later sections. The glove box was also modified to include high voltage (HV) and compressed air feed-through ports. An in-house power supply (Glassman High Voltage, NJ) was used for high voltage applications (not shown), which is capable of producing +5 kV with a 15 mA current rating. This was connected to the ESP cell 100 via a high voltage connection 114.

Feasibility Testing of ESP Collector Cell with BG Spores

Test results with BG spores showed the relationship of spore capture onto the collection plates vs. voltage for 0 V (control) and 2.5 kV. For both experiments, 600 ppm (by mass) of BG spores in DI water were nebulized with dry air to produce an aerosol flow rate of 3 LPM which was passed through the ESP collector for approximately 45 minutes. After collection, the removable collector plates were extracted from the ESP cell and placed into a Reflection-Absorption (R-A) optical assembly for IR spectral analysis. Optical microscopy of the collector plates was also performed, and spores of approximately 1 μm in size were readily observed on the plates that were operated at 2.5 kV as compared to the plates operated at 0 V. For the 2.5 kV test, spores were collected on both the ground and high voltage plates in approximately equal amounts, indicating that approximately equal populations of positively and negatively charged spores were entering the cell. Using an extinction coefficient derived in a separate experiment for the amide I band at ca. 1650 $cm^{-1}$, the spectrum corresponded to approximately $4\times10^7$ spores/$cm^2$ on the collection plates.

Relative Humidity Effects on ESP Collection efficiency

To test the effects of RH with respect to collection efficiency, the ESP collector was operated at 2.5 kV for two separate test conditions—one with and one without the diffusion drier, which resulted in RHs of approximately 35% and >60%, respectively, within the ESP collector. For both tests, a BG spore stock solution was aerosolized to produce a flow rate of 3 LPM for 45 minutes. Inclusion of the diffusion drier led to a substantial increase in the amount of spores collected, where the collection efficiency was calculated to increase by a factor of 10 when the drier was used.

Spore Collection vs. Applied Voltage

ESP cell collection of aerosolized BG spores was performed at different applied voltages to determine the effects of voltage with collection efficiency for the parallel plate cell design. All other collection parameters were held constant for each test (e.g. flow rate of 3 LPM, collection time of 30 minutes, and 5 mm gap distance between the plates, where the same stock solution was used for all tests). RA-IR spectra were obtained from the HV plates for three separate tests conducted at 0 kV, 2.5 kV, and 4.5 kV. The collection efficiency for these tests was calculated to be approximately 10% (2.5 kV) and 40% (4.5 kV). When calculating the collection efficiency, it is assumed that all of the spores leaving the nebulizer reach the ESP cell for collection. However, it has been observed that significant spore condensation/loss occurred between the nebulizer exhaust and the diffusion drier. In addition, a certain amount of spore condensation/loss within the diffusion drier was also expected. At the time of the experiments, we did not have the capability to quantify the amount of spore loss due to these effects, therefore the collection efficiencies stated above should be viewed as low end estimates, with the actual efficiencies likely being much higher.

Wire/Plate Collector Design

To concentrate airborne spores into a smaller region for throughput matching with an IR beam, an alternative design to the parallel plate ESP collector was investigated. The ESP collector cell was modified by spot welding a single tantalum wire (8 mil in diameter) to the ground plate and operated at high voltage. The wire protruded perpendicular to the ground plate and into the air stream approximately 2.5 mm, which was half of the gap distance between the HV and ground collector plates. Due to the highly localized electric field that was created between the wire and the HV plate, it was observed that the spores which were collected on the HV plate were concentrated into a much smaller area directly opposite the wire. The concentrated spores on ESP collector plate after collection were observed, with two different beam sizes that were used to collect R-A IR spectra of the collected spores. The larger beam had a diameter of 6.5 mm; the smaller beam was produced by an IR microscope and has a 0.5 mm diameter. The BG spot on the plate was approximately 3 mm in diameter and corresponded to approximately $2.5\times10^6$ total spores. Since the collected sample size was smaller than the size of the 6.5 mm beam, part of this beam's cross-sectional area was not utilized for spore probing and thus the detection signal was less than optimal. For the 0.5 mm diameter beam, however, the IR beam was condensed well within the sample size, therefore all of the cross-sectional area of this beam is utilized and a larger signal was produced for the same sample of BG spores.

For a truly throughput matched detection system, the collection area of the sample equals the cross-sectional area of the optical probe beam. Therefore, if the 0.5 mm beam were throughput matched with the collected sample, then only those spores contained within the collection area would be needed to produce the same spectrum, where the resulting spectrum would be at the same intensity i.e. 0.1 Absorbance for the largest peak. Considering that absorbance bands of $10^{-3}$ intensity are routinely detected with typical IR spectrometers, then a truly throughput matched detection system for this experiment would have a detection limit of approximately $10^3$ spores. By comparison, bioassay techniques require a minimum of $10^5$ spores for detection. Therefore, a bioaerosol collected via ESP methods that is throughput matched with an IR beam having a 0.5 mm diameter would have a detection limit that is 100 times better than a bioassay-based detection system.

Conclusions

An electrostatic precipitation (ESP) methodology for collecting airborne spores and microorganisms was been combined with in-situ optical analysis capabilities to provide a novel, real-time bioaerosol collection, detection, and identification system. A prototype ESP collector cell was fabricated and tested with aerosolized BG spores, where Reflection-Absorption IR analyses of the collector plates illustrated how spore collection and detection was accomplished. Furthermore, our results showed how ESP collection methods can be designed to optimize throughput matching with an optical probe beam to achieve spore detection limits that are 100 times lower than current bioassay techniques.

In accordance with the provisions of the patent statutes, the principle and mode of operation of this invention have been explained and illustrated in its preferred embodiments. However, it must be understood that this invention may be practiced otherwise than as specifically explained and illustrated without departing from its spirit or scope.

What is claimed is:

1. A detection system for particles suspended in a gas comprising:

an electrostatic precipitator constructed to collect the particles from the gas onto a collection surface using the force of an induced electrostatic charge on the particles, the electrostatic precipitator having a body and at least one electrode having a structure that focuses deposition of the particles in a defined area on the collection surface; and an optical probe coupled with the electrostatic precipitator and constructed to probe the particles with a beam in order to detect the particles;

the body of the electrostatic precipitator having a geometry that allows the beam to travel from the optical probe to the collection surface.

2. The detection system of claim 1 wherein the optical probe is selected from the group consisting of near, mid and far infrared probes, Raman probes using lasers from the ultraviolet to the near infrared region, ultraviolet light probes, visible light probes, fluorescent light probes, terahertz light probes, and laser probes.

3. The detection system of claim 2 wherein the optical probe is an infrared spectrometer.

4. The detection system of claim 1 wherein the beam travels to the collection surface in a reflection mode or a transmission mode.

5. The detection system of claim 1 which is able to detect any aerosolized particles including organic or inorganic particles.

6. The detection system of claim 5 which is able to detect particles that are airborne microorganisms and/or airborne bio-warfare agents.

7. The detection system of claim 1 wherein the geometry of the electrostatic precipitator body includes an access structure that allows the beam to travel to the collection surface.

8. The detection system of claim 7 wherein the access structure allows the beam to travel through the body.

9. The detection system of claim 8 wherein the access structure comprises a window in the body.

10. The detection system of claim 1 wherein the geometry of the electrostatic precipitator body allows the beam to travel directly from the optical probe to the collection surface.

11. The detection system of claim 1 wherein the structures of the electrostatic precipitator and the optical probe cooperate to allow real-time detection of the particles.

12. The detection system of claim 1 wherein the collection surface is located on the body of the electrostatic precipitator.

13. The detection system of claim 1 wherein the optical probe is able to identify the particles that are detected.

14. The detection system of claim 1 wherein the collection surface further comprises a moveable tape containing multiple different sections at which collection may occur.

15. The detection system of claim 1 further comprising an additional electrode and wherein the collection surface comprises the additional electrode or lies between the first electrode and the additional electrode.

16. The detection system of claim 4 wherein the beam travels to the collection surface in a reflection mode.

17. The detection system of claim 1 wherein the at least one electrode is a grid, a single wire, or any configuration of single wires.

18. A detection system for particles suspended in a gas comprising:

an electrostatic precipitator constructed to collect the particles from the gas onto a collection surface using the force of an induced electrostatic charge on the particles, the electrostatic precipitator having a body and including first and second electrodes, at least one of the electrodes having a structure that causes deposition of the particles in a defined area on the collection surface; and an optical probe coupled with the electrostatic precipitator and constructed to probe the particles with a beam in order to detect the particles;

the body of the electrostatic precipitator having a geometry that allows the beam to travel from the optical probe to the collection surface.

19. The detection system of claim 18 wherein the defined area substantially matches a cross-sectional area of the beam.

20. The detection system of claim 18 wherein the at least one electrode is a grid, a single wire, or any configuration of single wires.

21. The detection system of claim 18 wherein the first and second electrodes are oppositely charged or one of the electrodes charged and the other grounded.

22. The detection system of claim 18 wherein one of the electrodes is a collector electrode that functions as the collection surface.

23. The detection system of claim 18 wherein the geometry of the electrostatic precipitator body further allows the beam to reflect from the collection surface back to a detector.

* * * * *